(12) United States Patent
Gajda et al.

(10) Patent No.: US 8,926,830 B2
(45) Date of Patent: Jan. 6, 2015

(54) PROCESS FOR INCREASING AROMATICS PRODUCTION

(71) Applicant: UOP LLC, Des Plaines, IL (US)

(72) Inventors: Gregory J. Gajda, Mt. Prospect, IL (US); Mary J. Wier, Schaumburg, IL (US); Clayton Colin Sadler, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/856,349

(22) Filed: Apr. 3, 2013

(65) Prior Publication Data

US 2013/0225886 A1    Aug. 29, 2013

Related U.S. Application Data

(63) Continuation-in-part of application No. 13/417,181, filed on Mar. 9, 2012.

(60) Provisional application No. 61/480,838, filed on Apr. 29, 2011.

(51) Int. Cl.
| | |
|---|---|
| *C10G 35/04* | (2006.01) |
| *C10G 35/02* | (2006.01) |
| *C07C 2/00* | (2006.01) |
| *C10G 59/00* | (2006.01) |
| *C10G 59/06* | (2006.01) |

(52) U.S. Cl.
CPC . *C10G 35/02* (2013.01); *C07C 2/00* (2013.01); *C10G 59/00* (2013.01); *C10G 59/06* (2013.01); *C10G 2300/1044* (2013.01); *C10G 2400/02* (2013.01); *C10G 2400/30* (2013.01)
USPC ............ 208/134; 208/133; 208/137; 208/79; 208/80; 585/302; 585/300; 585/301; 585/407; 585/804

(58) Field of Classification Search
USPC ............... 208/62, 64–66, 134–138, 140, 143; 585/300, 301, 302, 303, 304, 312, 315, 585/319, 322, 407, 430, 800, 804, 805
See application file for complete search history.

(56) References Cited

U.S. PATENT DOCUMENTS

| 2,324,165 A | * | 7/1943 | Layng et al. | ..................... 208/79 |
|---|---|---|---|---|
| 2,380,279 A | * | 7/1945 | Welty, Jr. | ....................... 585/322 |

(Continued)

FOREIGN PATENT DOCUMENTS

| EP | 0184450 B1 | 11/1990 |
|---|---|---|
| EP | 0993500 B1 | 9/2002 |

OTHER PUBLICATIONS

Soderstrom, E.D., III, "Plant Energy Conservation: Computer Control for Energy Savings," Applied Automation Inc., Chem. Eng. Prog. v. 76 n. 8 60-62 (Aug. 1980), v. 76, n. 8, p. 60-62, Aug. 1980, ISSN: 03607275, Publisher: American Institute of Chemical Engineers (AIChE).

(Continued)

*Primary Examiner* — Walter D Griffin
*Assistant Examiner* — Jelitza Perez

(57) ABSTRACT

Processes for producing aromatics from a naphtha feedstream are provided. An exemplary process includes passing the feedstream to a fractionation unit, thereby generating a first stream including hydrocarbons having less than 8 carbon atoms and a second stream including hydrocarbons having at least 8 carbon atoms. The first stream is passed to a first reformer operated at a first set of reaction conditions to generate a first product stream. The first set of reaction conditions includes a first temperature and a first pressure. The second stream is passed to a second reformer operated at a second set of reaction conditions to generate a second product stream. The second set of reaction conditions includes a second temperature and a second pressure. The first pressure is lower than the second pressure.

19 Claims, 3 Drawing Sheets

(56) References Cited

U.S. PATENT DOCUMENTS

| | | | | |
|---|---|---|---|---|
| 2,697,684 A | * | 12/1954 | Hemminger et al. | 208/64 |
| 2,767,124 A | * | 10/1956 | Myers | 208/64 |
| 2,866,745 A | * | 12/1958 | Heinemann | 208/79 |
| 2,867,576 A | * | 1/1959 | Honeycutt | 208/65 |
| 4,401,554 A | * | 8/1983 | Choi et al. | 208/64 |
| 4,897,177 A | * | 1/1990 | Nadler | 208/79 |
| 6,004,452 A | * | 12/1999 | Ash et al. | 208/80 |
| 6,051,128 A | | 4/2000 | Nacamuli et al. | |
| 6,602,404 B2 | | 8/2003 | Walsh et al. | |
| 2007/0129590 A1 | | 6/2007 | Rhodey et al. | |
| 2012/0273392 A1 | | 11/2012 | Serban et al. | |
| 2012/0275974 A1 | | 11/2012 | Moser et al. | |
| 2012/0277500 A1 | | 11/2012 | Moser et al. | |
| 2012/0277501 A1 | | 11/2012 | Gajda et al. | |
| 2012/0277502 A1 | | 11/2012 | Gajda et al. | |
| 2012/0277503 A1 | | 11/2012 | Wegerer et al. | |
| 2012/0277504 A1 | | 11/2012 | Gajda et al. | |
| 2012/0277505 A1 | | 11/2012 | Serban et al. | |
| 2012/0277506 A1 | | 11/2012 | Negiz et al. | |
| 2012/0277507 A1 | | 11/2012 | Serban et al. | |
| 2012/0277508 A1 | | 11/2012 | Gajda et al. | |
| 2012/0277511 A1 | | 11/2012 | Moser et al. | |

OTHER PUBLICATIONS

Morrison, et al., "Advances in Process Control," Science v. 215 n. 4534 813-18 (Feb. 12, 1982), v. 215, n. 4534, p. 813-18, Feb. 12, 1982, ISSN: 00368075, Publisher: American Association for the Advancement of Science.

Fedorov, et al., "Catalytic Reforming With Simultaneous Production of High-Octane Fuel and Aromatic Hydrocarbons," Chemistry and Technology of Fuels and Oils, v. 8, n. 7-8, p. 569-572, Jul.-Aug. 1972, ISSN: 00093092.

Barker et al., Kirk-Othmer Encyclopedia of Chemical Technology. Petroleum. 2005, pp. p. 40, figure 4 and figure 5.

U.S. Appl. No. 13/327,164, filed Dec. 15, 2011, Moser.
U.S. Appl. No. 13/327,200, filed Dec. 15, 2011, Moser.
U.S. Appl. No. 13/327,143, filed Dec. 15, 2011, Moser.
U.S. Appl. No. 13/327,212, filed Dec. 15, 2011, Moser.
U.S. Appl. No. 13/327,220, filed Dec. 15, 2011, Moser.
U.S. Appl. No. 13/327,185, filed Dec. 15, 2011, Serban.
U.S. Appl. No. 13/327,178, filed Dec. 15, 2011, Serban.
U.S. Appl. No. 13/327,170, filed Dec. 15, 2011, Serban.
U.S. Appl. No. 13/327,192, filed Dec. 15, 2011, Serban.

* cited by examiner

PROCESS FOR INCREASING AROMATICS PRODUCTION

CROSS-REFERENCE TO RELATED APPLICATIONS

This application is a continuation-in-part of U.S. patent application Ser. No. 13/417,181, filed Mar. 9, 2012, which claims the benefit of U.S. Provisional Application No. 61/480,838, filed Apr. 29, 2011.

TECHNICAL FIELD

The technical field generally relates to the process of enhancing the production of aromatic compounds. More particularly, the technical field relates to the improvement and enhancement of aromatic compounds such as benzene, toluene and xylenes from a naphtha feedstream.

BACKGROUND

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

The upgrading of gasoline is an important process, and improvements for the conversion of naphtha feedstreams to increase the octane number have been presented in U.S. Pat. Nos. 3,729,409, 3,753,891, 3,767,568, 4,839,024, 4,882,040 and 5,242,576. These processes involve a variety of means to enhance octane number, and particularly for enhancing the aromatic content of gasoline.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. Nos. 4,677,094, 6,809,061 and 7,799,729. However, there are limits to the methods and catalysts presented in these patents, and which can entail significant increases in costs.

BRIEF SUMMARY

Processes for producing aromatics from a naphtha feedstream are provided herein. In an embodiment, a process for producing aromatics from a naphtha feedstream includes passing the feedstream to a fractionation unit, thereby generating a first stream that includes hydrocarbons having less than 8 carbon atoms and a second stream that includes hydrocarbons having at least 8 carbon atoms. The first stream is passed to a first reformer to generate a first product stream. The first reformer is operated at a first set of reaction conditions, and the first set of reaction conditions includes a first temperature and a first pressure. The second stream is passed to a second reformer to generate a second product stream. The second reformer is operated at a second set of reaction conditions, and the second set of reaction conditions includes a second temperature and a second pressure. The first pressure is lower than the second pressure. The first product stream and the second product stream are passed to an aromatics separation unit.

In another embodiment, a process for producing aromatics from a naphtha feedstream includes passing the feedstream to a fractionation unit, thereby generating a first stream that includes hydrocarbons having less than 8 carbon atoms and a second stream that includes hydrocarbons having at least 8 carbon atoms. The first stream is passed to a first reformer to generate a first product stream. The first reformer is operated at a first set of reaction conditions, and the first set of reaction conditions includes a first temperature, a first pressure, a first hydrogen to hydrocarbon feed ratio, and a conversion per pass for hydrocarbons having 6 carbon atoms. The second stream is passed to a second reformer to generate a second product stream. The second reformer is operated at a second set of reaction conditions, and the second set of reaction conditions includes a second temperature, a second pressure, and a second hydrogen to hydrocarbon feed ratio. The first temperature is greater than the second temperature, the first pressure is lower than the second pressure, and the second hydrogen to hydrocarbon feed ratio is greater than the first hydrogen to hydrocarbon feed ratio. The first product stream and the second product stream are passed to an aromatics separation unit.

In another embodiment, a process for producing aromatics from a naphtha feedstream includes passing the feedstream to a fractionation unit, thereby generating a first stream that includes hydrocarbons having less than 8 carbon atoms and a second stream that includes hydrocarbons having at least 8 carbon atoms. The first stream is passed to a first reformer to generate a first product stream. The first reformer is operated at a first set of reaction conditions, and the first set of reaction conditions includes a first temperature and a first pressure. The second stream is passed to a second reformer to generate a second product stream. The second reformer is operated at a second set of reaction conditions, and the second set of reaction conditions includes a second temperature and a second pressure. The first temperature is greater than the second temperature and the first pressure is lower than the second pressure. The first product stream is passed to a compressor. The first product stream and the second product stream are passed to an aromatics separation unit. The first product stream is passed to the aromatics separation unit from the compressor and the second product stream is passed to the aromatics separation unit in the absence of further pressurizing.

DETAILED DESCRIPTION

Figure 1:
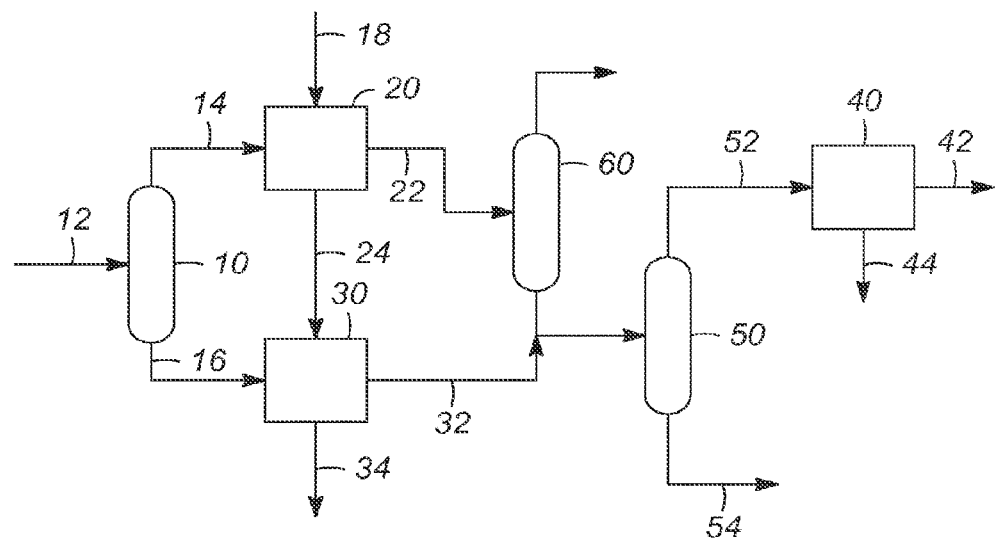
FIG. 1 is one embodiment of the invention showing a first split feed process.

The following detailed description is merely exemplary in nature and is not intended to limit the invention or the application and uses of the invention. Furthermore, there is no intention to be bound by any theory presented in the preceding background or the following detailed description.

The present invention is directed to improving the yields of aromatics from a hydrocarbon feedstream. In particular, the improvement is for a naphtha feedstream where the hydrocarbons are reformed to increase the yields of aromatics in the C6 to C8 range. The new process is designed to utilize a single catalyst, rather than a more expensive process that includes multiple catalysts.

In hydrocarbon processing, reforming is used to improve the quality of a hydrocarbon feedstock, and in particular a naphtha feedstock. The feedstock comprises many compounds and the reforming process proceeds along numerous pathways. The reaction rates vary with temperature, and the Arrhenius equation captures the relationship between the reaction rate and temperature. The reaction rate is controlled by the activation energy for a particular reaction, and with the many reactions in the reforming process, there are many, dissimilar activation energies for the different reactions. For the different reactions, it is possible to manipulate the conversion of one hydrocarbon to a desired product, e.g. hexane to benzene. While using the same catalyst, the reactions can be manipulated through changing the temperature, pressure, and hydrogen to hydrocarbon ratios under which the reactions are carried out. This manipulation is further enhanced by, at least, a partial separation of the components within the naphtha mixture into separate feeds. The different feeds can then be processed to enhance selectivity control to the desired product, or in this case to the production of aromatics in the C6 to C8 range.

The reforming process is substantially endothermic, and as such a substantial amount of heat is added to maintain the temperature of reaction. Different components within the naphtha mixture have a greater endothermicity during the dehydrogenation process. The present invention is aimed at separating the process into at least two reaction zones, where one zone is substantially isothermal, and another zone is operated with a non-isothermal temperature profile. The non-isothermal zone includes a feed stream that is made up of hydrocarbon components that are converted to a product through highly endothermic catalytic reforming reactions, and which result in a significant temperature decrease in the reaction zone. Examples include naphthenic compounds converted to aromatics. The isothermal reaction zone includes a feed that while the components can have different activation energies, the reactions are relatively low endothermic catalytic reforming reactions, and are favored at high temperatures. The process can include passing the effluent stream from the non-isothermal zone to the isothermal zone, as the components having high endothermicity will have predominantly reacted in the non-isothermal zone. Alternatively, the effluent stream from the non-isothermal zone may be separately passed to an aromatics separation unit, with optional intervening unit operations between the isothermal zone and the aromatic separation unit. For example, as described in further detail below, the isothermal zone is operated at a lower pressure than the non-isothermal zone, and hydrogen recovery is generally conducted at pressures that are greater than the pressure at which the isothermal zone is operated. As such, the effluent stream from the isothermal zone may be passed to a compressor to increase pressure thereof and to remove hydrogen therefrom prior to passing to the aromatics separation unit, whereas no such increase in pressure may be necessary for the effluent stream from the non-isothermal zone may be necessary.

One aspect of the present invention was the discovery that the designs go against the belief of longer processing times with hydrocarbon components that are the most difficult to reform. In particular, it is more difficult to reform C6s to aromatics than to reform C7s and higher components. Therefore, one would suspect that the C6 compounds should have a greater contact time with the catalyst than C7 and higher components. Studies have found the reverse to be true. The C6 compounds need a relatively short contact time. This is counter intuitive, and the process turns the general idea upside down when processing separate components. This leads to several features for various designs, including separating and processing at higher temperatures.

One consideration when processing hydrocarbons in a reformer is the balancing of reaction conditions. In a reformer there are competing reactions. The reactions take place at different rates due to differing activation energies and other factors. It has been found that increasing the temperature for some of the reforming reactions with lighter hydrocarbons favors the dehydrogenation and cyclization of hydrocarbons over other less favorable reactions, such as catalytic cracking. However, the temperature must also be low enough to prevent thermal cracking from occurring to any significant extent. Lowering the hydrogen to hydrocarbon ratio or the pressure will reduce the temperature that is necessary to optimize the relative reaction rates, especially for hydrocarbons having less than 8 carbon atoms.

For purposes of the description of the reactions, there are several reactions that occur in a reformer. The principal ones include dehydrogenation and cyclization, and as used hereinafter, the use of the term dehydrogenation is intended to include cyclization.

One embodiment of the invention is a process for producing aromatics from a hydrocarbon feedstream, as shown in FIG. 1. The process includes passing the hydrocarbon feedstream 12 to a fractionation unit 10 to generate a first stream 14 that includes hydrocarbons having less than 8 carbon atoms and a second stream 16 that includes hydrocarbons that have at least 8 carbon atoms. In particular, the first stream 14 includes the hydrocarbons having less than 8 carbon atoms as the majority of the first stream 14, although it is to be appreciated that trace amounts (e.g., less than 10 mol %, such as less than 1 mol %, based on the total amount of the first stream 14) of hydrocarbons having at least 8 carbon atoms can be present in the first stream 14. Likewise, the second stream 16 includes the hydrocarbons having at least 8 carbon atoms as the majority of the second stream 16, although it is to be appreciated that trace amounts (e.g., less than 10 mol %, such as less than 1 mol %, based on the total amount of the second stream 16) of hydrocarbons having less than 8 carbon atoms can be present in the second stream 16. The first stream 14 has a reduced concentration of endothermic hydrocarbon components, and the second stream 16 has an increased concentration of endothermic components. The first stream 14 is passed to a first reformer 20, and creates a first reformer effluent stream 22. The first reformer 20 is operated at a first set of reaction conditions, including a first temperature and a first pressure. The second stream 16 is passed to a second reformer 30, and creates a second reformer effluent stream 32. The second reformer 30 is operated at a second set of reaction conditions, including a second temperature and a second pressure. The first pressure is lower than the second pressure. Lower pressure enables higher selectivity to aromatics to be achieved at lower temperatures than would otherwise be required for n-C6 and methyl cyclopentane (MCP), thereby achieving desired selectivity while minimizing coke formation. In an embodiment, the first temperature is greater than the second temperature, although it is to be appreciated that the first temperature and the second temperature may be the same or the second temperature may be higher than the first temperature under some circumstances where the first temperature is at a lower value within a range of suitable first temperatures and the second temperature is at a higher value within a range of suitable second temperatures, as described in further detail below. In this manner, the first reformer is operated to minimize pressure, thereby creating conditions for maximizing benzene and toluene conversion from the hydrocarbons that have less than 8 carbon atoms in the first stream 14. The first reformer effluent stream 22 and the second reformer effluent stream 32 are passed to an aromatics separation unit 40. The aromatics separation unit 40 creates an aromatics product stream 42 and a raffinate stream 44 that is lean in aromatic compounds. The first and second reformers 20, 30 use the same catalyst for reforming the hydrocarbon feeds to the reformers.

While it has been found that the hydrocarbon feed can be separated and sent to different reformers, the operation and practice use different catalysts, such as presented in U.S. Pat. No. 4,882,040 to R. M. Dessau, et al., and which is incorporated by reference in its entirety. The present invention has found that one can use a single type of catalyst, such as one is normally used in reforming. This presents a savings in that the catalyst needs only a single regenerator, where both catalyst streams are passed to the single, common regenerator.

The present invention has found that with split feeds, the operating conditions are different to generate an improvement in yields. In this process, the first temperature may be greater than the second temperature. In an embodiment, the first temperature is greater than 530° C. For example, in a specific embodiment, the first temperature is from about 530° C. to about 580° C., such as from about 545° C. to about 560° C. Within the context of the instant application, the term "about" is intended to mean that the temperature may vary by insubstantial amounts from the endpoints specified, such as by one degree or less. Also in this embodiment, the second temperature is less than 540° C., and may be kept to a value less than the first temperature. For example, in a specific embodiment, the second temperature is from about 520° C. to about 540° C., such as from about 530° C. to about 540° C. While the process operates reformers at targeted reaction temperatures, the process is endothermic, and the temperatures in the reactors generally will drop as the reaction proceeds. Therefore, the temperature at the inlet of the reactor is generally the highest temperature, and is the temperature that is controlled. For purposes of this description, the terms 'reaction temperature' can be used interchangeably with 'inlet temperature' and when the term 'reaction temperature' is used, it is intended to mean the temperature at the inlet conditions of the reactor.

As alluded to above, the first pressure is lower than the second pressure, which enables the first reformer 20 to operate under conditions that promote conversion of hydrocarbons having less than 8 carbon atoms, especially n-C6 and methyl cyclopentane, to benzene and toluene at lower temperatures than would otherwise be required to achieve equivalent conversion rates. For example, in an embodiment, the first pressure is from about 130 to about 310 kPa, and the second pressure is from about 240 to 580 kPa, provided that the first pressure is less than the second pressure. Hydrogen to hydrocarbon feed ratios also impact conversion of the hydrocarbons in the first stream 14 to aromatics, with lower hydrogen to hydrocarbon feed ratios correlating to increased aromatics selectivity for n-C6 and MCP. Lower hydrogen to hydrocarbon feed ratios also enable more heat to be carried into the reformer by providing additional heat capacity in the feedstream, thereby assisting with maintaining temperatures in the reformer to be kept closer to isothermal conditions. In an embodiment, the first set of reaction conditions at which the first reformer 20 is operated includes a first hydrogen to hydrocarbon feed ratio and the second set of reaction conditions at which the second reformer 30 is operated includes a second hydrogen to hydrocarbon feed ratio. In an embodiment, the second hydrogen to hydrocarbon feed ratio is greater than first hydrogen to hydrocarbon feed ratio. It has been discovered that hydrogen to hydrocarbon feed ratios materially impact aromatics yields in the first reformer, whereas hydrogen to hydrocarbon feed ratios in the second reformer are of lesser impact. In an embodiment, the first hydrogen to hydrocarbon feed ratio is a mole ratio of from about 0.1 to about 10, such as from about 0.2 to about 2, or from about 0.2 to about 1.2. In an embodiment, the second hydrogen to hydrocarbon feed ratio is a mole ratio of from about 0.5 to about 10, such as from about 5, or such as from about 1.2 to about 2.5.

In an embodiment, the first set of conditions further includes a conversion per pass rate for hydrocarbons that have 6 carbon atoms, which is a variable that affects coke formation on the catalyst. For example, in an embodiment, the conversion per pass rate for the hydrocarbons that have 6 carbon atoms is from about 33% to about 50%, by mol. Conversion per pass rates above 50% may cause severe catalyst deactivation, leading to poor selectivity for aromatic conversion from the hydrocarbons having 6 carbon atoms. However, conversion per pass rate for the hydrocarbons that have 6 carbon atoms of less than about 33% results in excessive raffinate from the aromatics separation unit and excessive recycle stream volume.

The invention separates the hydrocarbon feedstream into the first stream 14 which has a reduced naphthene content, and comprises C7 and lighter hydrocarbons. In a preferred embodiment, the hydrocarbon feedstream is a naphtha feedstream. The naphtha feedstream is also separated into the second stream 16 which has a relatively increased naphthene content. The second stream 16 includes C8 and greater hydrocarbons, and C6 and C7 naphthenic compounds. The reduced naphthene content allows for operation of the first reformer 20 at reaction conditions that will also minimize the temperature drop during the reforming process. The reformer dehydrogenates the hydrocarbons, which is an endothermic process, and has components in the hydrocarbon stream that absorb more heat than other components. By separating the more endothermic compounds from the first stream 14, the first reformer can be operated at a higher temperature on average. The naphtha feedstream can be split to optimize operation of the two reformers, and can depend on the makeup of the naphtha feedstream.

It has been found that hydrocarbons in the first stream, such as MCP, n-C6, and n-C7, have a greater tendency to form coke on catalysts than hydrocarbons in the second stream. Despite the higher rates of coke formation that are attributable to n-C6 and methyl cyclopentane, reaction temperatures of at least 530° C. have been found to provide higher conversion rates of n-C6 and MCP to benzene and toluene, as described above. By splitting the feedstream into the first stream that includes the hydrocarbons having less than 8 carbon atoms and the second stream that includes the hydrocarbons having at least 8 carbon atoms, hydrocarbon species that exhibit higher rates of coke formation as reaction temperatures increase are segregated to the first reformer where process design can account for the higher rates of coke formation, whereas the second reformer may be operated at different process conditions without concern of excessive coke formation. For example, the first reformer may include at least two reactors, with the first stream further split and separately passed through the individual reactors to minimize residence time of the first stream in the first reformer and to enable higher rates of catalyst cycling. In this manner, higher rates of coking can be offset by higher rates of catalyst cycling to avoid adverse impact on aromatics conversion attributable to catalyst deactivation.

The process involves the parallel flow of the hydrocarbon process streams through the reformers. The catalyst can flow in parallel, or in series through the reformers. A parallel process flow of the catalyst includes the splitting of a catalyst stream from the regenerator into a plurality of catalyst feedstreams, and passing one of the catalyst feedstreams to each reformer. A series flow of the catalyst includes the passing of the catalyst from the regenerator to a first reformer, and passing catalyst from the first reformer to the second reformer. As shown in FIG. 1, a series flow of catalyst is presented with a fresh catalyst stream 18 passing to the first reformer 20. A partially spent catalyst stream 24 is passed from the first reformer 20 to the second reformer 30, and a spent catalyst stream 34 is returned to the regenerator. This process can be continued for subsequent reactors in the process.

As presented herein, the reformer is a reactor that can comprise a plurality of reactor beds, and is intended to incorporate the use of multiple reactor beds within the scope of the invention. The reformer can also include interbed heaters, wherein the process reheats catalyst and/or the process stream as the catalyst and process stream flow from one reactor bed to a sequential reactor bed within the reformer. The most common type of interbed heater is a fired heater that heats the fluid and catalyst flowing in tubes. Other heat exchangers can be used.

A particular reforming reactor is one that performs a high temperature endothermic catalytic reaction for the cyclization and dehydrogenation of hydrocarbons. This reformer increases the aromatics content of a naphtha feedstream, and generates a hydrogen stream also. In particular, the reformer is used for production of benzene, toluene and xylenes.

The process can further include a light gas separation unit 60 for processing the effluent stream from the reformers. The light gas separation unit 60 is typically a light fractionator for the separation of lighter gases from the effluent streams from the reformers. The first reformer 20 is operated at more severe conditions and generated more light gases.

The light gas separation unit 60 can be a debutanizer, or a depentanizer for removing C4 and lighter gases, or C5 and lighter gases respectively. The choice of a debutanizer or depentanizer can depend on the desired content of the effluent stream 22 to be passed to the aromatics separation unit 40.

Another embodiment comprises passing a naphtha feedstream 12 to a fractionation unit 10, generating an overhead stream 14 comprising C6 and C7 hydrocarbons, and a bottoms stream 16 comprising hydrocarbons having at least 8 carbon atoms. The overhead stream has a relatively reduced naphthenic component content, and the bottoms stream has a relatively increased naphthenic component content. The overhead stream 14 is passed to a first reformer 20 operated at a first set of reaction conditions. The first reformer 20 includes a catalyst inlet and a catalyst outlet for receiving a catalyst stream 18 and passing partially spent catalyst out 24. The bottoms stream 16 is passed to a second reformer 30 where the second reformer 30 has a catalyst inlet for receiving a catalyst stream 24 from the first reformer 20 and a catalyst outlet for passing a catalyst stream 34 to a regenerator.

The first reformer is operated at a temperature of at least 530° C. and the second reformer is operated at a temperature below 540° C. The first stream is processed in the first reformer 20 under more severe conditions, while the residence time within the first reformer 20 is less than the residence time for the second stream in the second reformer 30. The reduced residence time in the first reformer 20 can be accomplished through use of two or more reactors in the first reformer 20, as set forth above.

The first reformer 20 generates an effluent stream 22 which is passed to a reformate splitter 50. The second reformer 30 generates an effluent stream 32 which, in an embodiment, is passed to the reformate splitter 50, although it is to be appreciated that the effluent streams 22, 32 from the first reformer 20 and the second reformer 30, respectively, may be maintained separate up to introduction into an aromatic separation unit 40. The reformate splitter 50 generates a reformate overhead stream 52 comprising C6 to C7 aromatics. The overhead stream 52 is passed to the aromatics separation unit 40, and generates an aromatics product stream 42 and a raffinate stream 44. The raffinate stream 44 is lean in aromatics. The reformate splitter 50 generates a bottoms stream 54 comprising aromatics having at least 8 carbon atoms. The reformate bottoms stream is passed to an aromatics complex for utilizing the aromatics components that have at least 8 carbon atoms.

The aromatics separation unit 40 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art.

Figure 2:
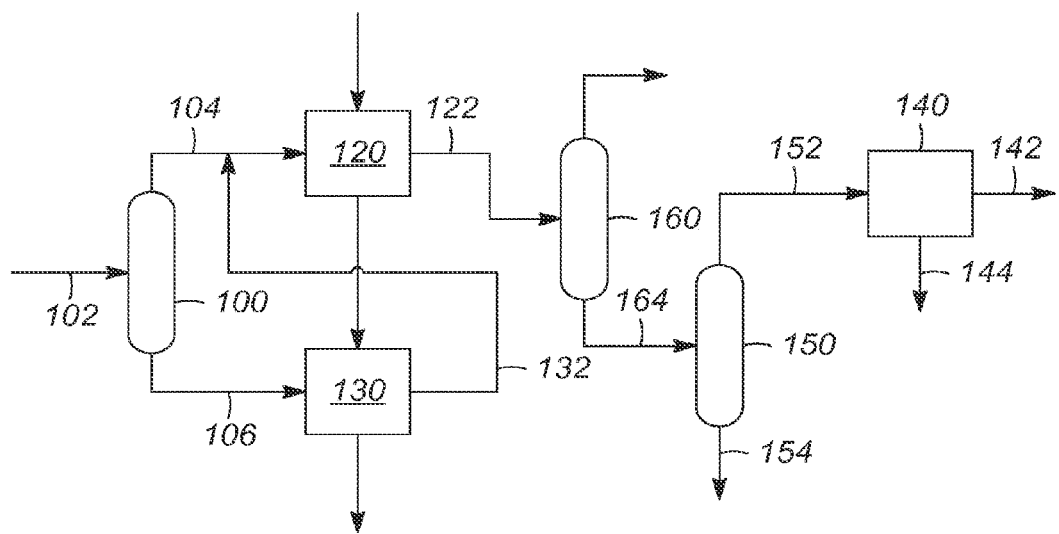
FIG. 2 is a second embodiment of the invention showing a second split feed process.

The processing of a mixture of hydrocarbons to generate aromatics can require a better understanding of the chemistry, which can lead to counter-intuitive results. When processing a hydrocarbon feedstream, the feedstream is separated to take advantage of differences in the chemistry of the different hydrocarbon components. One aspect of the present invention is shown in FIG. 2. A process for producing aromatics from a hydrocarbon stream 102 includes passing the hydrocarbon stream to a fractionation unit 100. The fractionation unit 100 generates an overhead stream 104 comprising hydrocarbons having less than 8 carbon atoms and having a reduced concentration of endothermic compounds. The unit 100 also generates a bottoms stream 106 comprising hydrocarbons that have at least 8 carbon atoms and that have an increased concentration of endothermic compounds. The use of the term endothermic compounds refers to hydrocarbons that exhibit strong endothermicity during the dehydrogenation process. While many compounds might exhibit some endothermicity, the endothermic compounds comprise primarily naphthenic compounds, and are those compounds that are characterized with a strong tendency to reduce the temperature of the reactor during the dehydrogenation and cyclization process in the reformers. For purposes of discussion hereinafter, endothermic compounds refer to naphthenes and compounds with similar endothermicities.

The overhead stream 104 is passed to a first reformer 120, where the first reformer 120 is operated at a first temperature. The bottoms stream 106 is passed to a second reformer 130, where the second reformer 130 is operated at a second temperature, and generates a second reformer effluent stream 132. In an embodiment, the second reformer effluent stream 132 is passed to the first reformer 120, where the overhead stream 104 and the second reformer effluent stream 132 are processed to generate a first reformer effluent stream 122. The first reformer effluent stream 122 is passed to an aromatics separation unit 140 and generates an aromatics product stream 142 and a raffinate stream 144. The process uses the same catalyst for the reformers, which in turn saves through having only a single, common regenerator. The regenerator receives the spent catalyst and can pass regenerated catalyst to one or more of the reformers. The catalyst can also be passed from the first reformer 120 to the second reformer 130 in a cycle of using fresh catalyst in the first reformer 102, passing partially spent catalyst to the second reformer 130, and passing spent catalyst back to the regenerator.

The first reformer 120 is for operating at more severe conditions than the second reformer 130. Hydrocarbons that have less than 8 carbon atoms can be processed in a reformer at higher temperatures, but with a lower residence time. The first reformer temperature is greater than 530° C. The second reformer temperature is preferred to be less than 540° C.

The hydrocarbon feedstream can be a naphtha feedstream, and the fractionation unit 100 separates the hydrocarbon feedstream into a first stream which comprises hydrocarbons having less than or equal to 7 carbon atoms, or be operated to comprise hydrocarbons having less than or equal to 6 carbon atoms. The fractionation unit 100 generates a bottoms stream that includes hydrocarbons having at least 8 carbon atoms The process can include passing the first reformer effluent stream 122 to a reformate splitter 150. The reformate splitter 150 generates an overhead stream 152 comprising hydrocarbons having less than 8 carbon atoms including C6 to C7 aromatic compounds, and a bottoms stream 154 comprising aromatic compounds having at least 8 carbon atoms and other hydrocarbons that have at least 8 carbon atoms.

The process can further include a light gas separation unit 160. The light gas separation unit 160 separates hydrogen and hydrocarbons having less than 6 carbon atoms in the effluent stream from the reformers. In particular, the light hydrocarbon separation unit 160 separates hydrocarbons having less than 6 carbon atoms from the first reformer effluent stream 122, creating an overhead stream 162 comprising butanes and compounds having less carbon atoms than butanes or pentanes and compounds having less carbon atoms than pentanes. In particular, C1 to C4 hydrocarbon compounds are undesirable and occupy volume or interfere with reactions and separations downstream. The removal of the hydrocarbons having less than 6 carbon atoms reduces downstream costs and equipment. The bottoms stream 164 from the light hydrocarbon separation unit 160 is passed to the reformate splitter 150. Some of the hydrocarbons in the overhead stream 162 may optionally be recycled to the first reformer 120 by combining with the overhead stream 104 to lower the hydrogen to hydrocarbon ratio in the first reformer 120 while providing additional heat capacity to reduce the magnitude of the reaction endotherm.

The raffinate stream 144 leaving the aromatics separation unit 140 comprises hydrocarbons in the C6 to C8 range, which are components that are susceptible to reforming. The raffinate stream 144 can be recycled to the either reformer 120, 130, with a preference to recycle the raffinate stream 144 to the first reformer 120.

Figure 3:
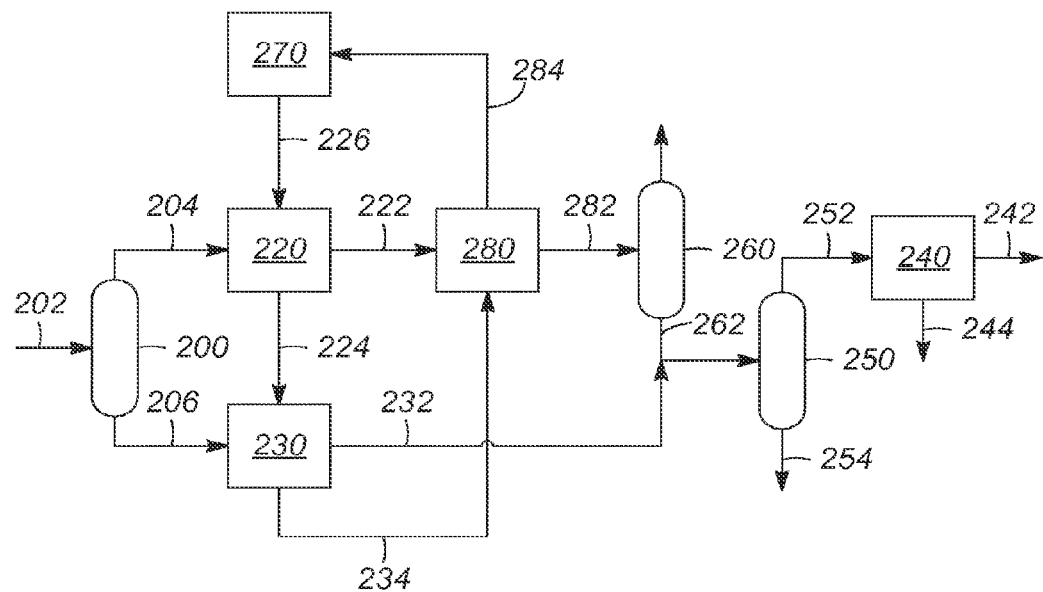
FIG. 3 is a third embodiment showing a third split feed process.

An alternate embodiment involves a separate design of the process, as shown in FIG. 3. The process includes passing a naphtha feedstream 202 to a fractionation unit 200. The fractionation unit 200 generates a first stream 204 passing out the overhead of the fractionation unit 200 and a second stream 206 passing out the bottom of the fractionation unit 200.

The first stream 204 is passed to a first reformer 220, where the first reformer 220 has a catalyst inlet stream 226 comprising regenerated catalyst. The first reformer 220 has a catalyst outlet 224 and a first reformer effluent stream 222. The second stream 206 is passed to a second reformer 230 and generates a second reformer effluent stream 232. The second reformer 230 has a catalyst inlet stream 224 which is passed from the first reformer 220, and a catalyst outlet stream 234. The spent catalyst in the catalyst outlet stream 234 is passed to a regenerator 270, wherein the catalyst is regenerated and recycled to the first reformer 220. The first reformer effluent stream 222 and the second reformer effluent stream 232 are passed to an aromatics separation unit 240 for the recovery of aromatics.

The aromatics separation unit 240 generates a purified aromatics stream 242 and a raffinate stream 244 comprising hydrocarbon components that can be recycled. The process of this embodiment uses at least two reactors for the second reformer 230 where the second stream 206 passes sequentially through the reactors, with the process stream heated as it passes between the reactors with heat exchangers.

In an alternate variation of this embodiment, the process further includes passing the first reformer effluent stream 222 to a third reformer 280 operated at a third set of reaction conditions. The third reformer 280 generates a third effluent stream 282 and the third reformer effluent stream is passed to the aromatics separation unit 240. The third reformer effluent stream can be passed to the reformate splitter 250 prior to passing to the aromatics separation unit 240. The third reformer effluent stream 282 can also be passed to a light hydrocarbon fractionation unit 260 for separating out butanes/pentanes and hydrocarbons having less carbon atoms than butanes prior to passing the process stream 262 to the aromatics separation unit 240.

The third set of reaction conditions includes a third temperature, where the third temperature is greater than the reaction temperature in the second reformer 230. The catalyst outlet stream 234 is passed from the second reformer 230 to the third reformer 280. The catalyst is partially spent upon entry to the third reformer 280, and is heated to a third reformer inlet temperature. The catalyst after being used in the third reformer 280 is passed as a spent catalyst stream 284 to the regenerator 270.

The third reformer effluent stream 282, after passing through the light hydrocarbon fractionation unit 260, passes the process stream to a reformate splitter 250. The second reformer effluent stream 232 is also passed to the reformate splitter 250. The reformate splitter 250 generates an overhead stream 252 comprising C6 to C7 aromatic compounds and a bottoms stream comprising aromatic compounds having at least 8 carbon atoms. The overhead stream 252 is passed to the aromatics recovery unit 240 where xylenes, benzene and toluene are recovered 242. A raffinate stream 244 comprising non-aromatic compounds is also generated, and can be recycled to one of the reformers.

The first reformer 220 operating temperature is greater than 530° C. The second reformer 230 operating temperature is less than 540° C., and the third reformer 280 operating temperature is greater than 540° C.

The naphtha feedstream 202 is divided into a first stream comprising hydrocarbons having less than 8 carbon atoms, e.g., hydrocarbons having up to 7 carbon atoms, and a second stream comprising hydrocarbons having at least 8 carbon atoms. The first stream will preferably have a lower relative naphthenic content, and a lower content of compounds with relatively high endothermicity. The second stream will preferably have a higher relative naphthenic content, and a relatively increased content of compounds with relatively high endothermicity.

The reforming process is an endothermic process, and the reformers 220, 230, 280 can comprise multiple reactor beds with interbed heaters. The reactor beds are sized with the interbed heaters to maintain the temperature of the reaction in the reactors. A relatively large reactor bed will experience a significant temperature drop, and can have adverse consequences on the reactions. Likewise, between reformers, such as the first reformer 220 and the third reformer 280, there can be an inter-reformer heater to heat the process stream to a desired inlet temperature. The catalyst can also pass through inter-reformer heaters to bring the catalyst up to the desired reformer inlet temperatures.

Figure 4:
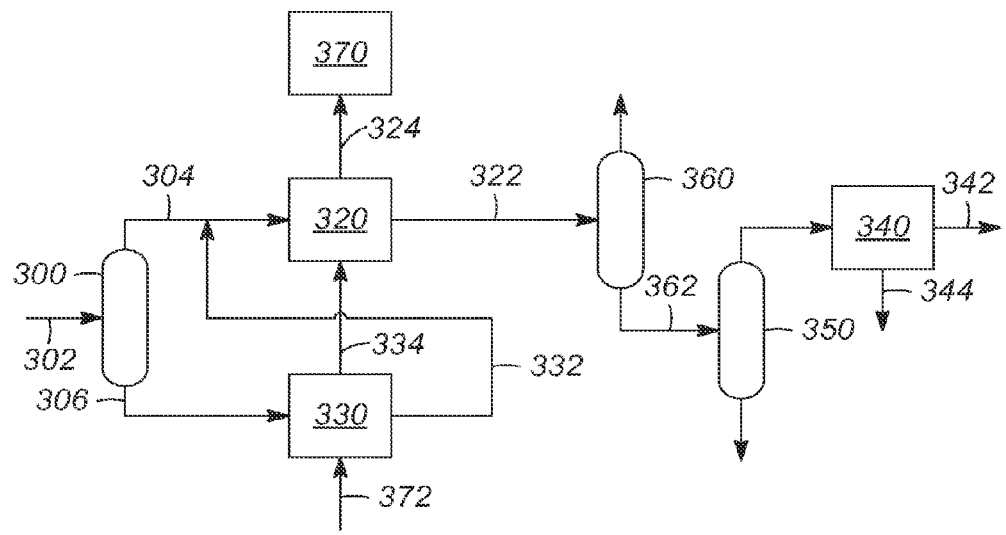
FIG. 4 is a fourth embodiment showing a fourth process with a split naphtha feed.

Another embodiment, as shown in FIG. 4, involves a process for producing an aromatics product stream from a naphtha feedstream. The naphtha feedstream 302 is passed to a fractionation unit 300 and generates an overhead stream 304 comprising hydrocarbons having less than 8 carbon atoms and a bottoms stream 306 comprising hydrocarbons having at least 8 carbon atoms. The first stream 304 is passed to a first reformer 320 and is operated at a first set of reaction conditions to generate a first product stream 322. The second stream 306 is passed to a second reformer 330, and is operated at a second set of reaction conditions to generate a second product stream 332. The second product stream 332 is passed to the first reformer 320, where the second product stream mixes with the first stream 304. The combined stream is passed to the first reformer 320 to generate the first product stream 322. The first product stream 322 is passed to an aromatics separation unit 340 to generate a purified aromatics product stream 342 and a raffinate stream 344.

The catalyst used in this embodiment is passed through the both reformers with fresh, or regenerated, catalyst passed to the second reformer 330 as a catalyst inlet stream at a second reformer inlet temperature. The catalyst is partially spent when leaving the second reformer 334 and is passed to the first reformer 320. The catalyst is heated to a first reformer catalyst inlet temperature, and the catalyst may be heated to a greater temperature when entering the first reformer 320, than when entering the second reformer 330. The first reformer 320 generates a spent catalyst stream 324 which passes the spent catalyst to a regenerator 370.

The reformers 320, 330 can each comprise a plurality of reactors. A preferred number of reactors is from 2 to 5 reactors, where the catalyst and process stream flow sequentially through the reactors. In between the reactors, the catalyst and process stream are heated in inter-stage heaters to bring the temperature of the catalyst and process stream back to the reformer inlet temperatures.

The process involves using the same catalyst in different reformers where the reformers are operated under different operating conditions. The primary operational difference is the inlet temperatures of the reformers and the operating pressures within the reformers. The process generates a first stream 304 from the fractionation unit 300 that comprises hydrocarbons having 6 or less carbon atoms, and is passed to the first reformer 320. The first stream 304 will preferably be generated with a relatively reduced naphthene content to reduce the endothermicity of the first stream 304. The first reformer 320 is operated at a first set of reaction conditions that includes a first reaction temperature. The first reaction temperature is greater than 530° C., while the second reaction temperature is less than 540° C.

The processing conditions of the different reformers allows for different operational control. Additional variables that are controllable include the space velocities, the hydrogen to hydrocarbon feed ratios, and the pressures. It is preferred that the pressure in the first reformer with the hydrocarbons having less than 8 carbon atoms is operated at a lower pressure than in the reformer with the hydrocarbons having at least 8 carbon atoms. An example for operating pressures for the first reformer are from 130 kPa to 310 kPa with a preferred pressure of around 170 kPa (10 psig), and operating pressures for the second reformer are from 240 kPa to 580 kPa with a preferred pressure of around 450 kPa (50 psig).

The fractionation unit 300 also generates a second stream 306 that is passed to a second reformer 330. The second stream 306 comprises hydrocarbons having at least 8 carbon atoms, and the second stream 306 will preferably have a relatively increased naphthene content.

Figure 5:
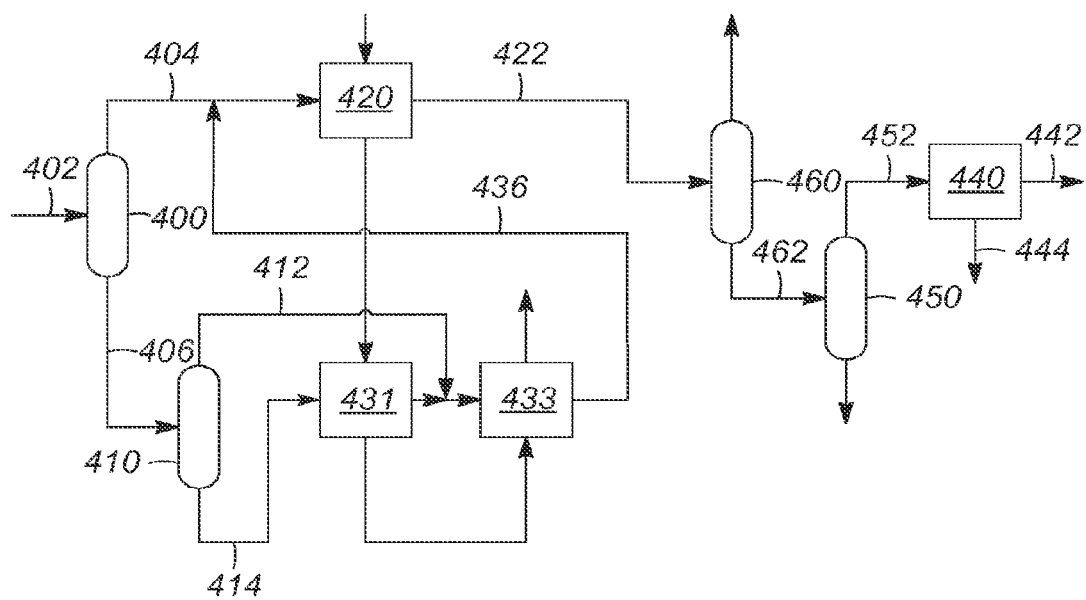
FIG. 5 is a fifth embodiment showing a fifth process with an additional split feed.

The process can further comprise separating the second stream into an intermediate stream and a heavy stream, with the heavy stream including a majority of hydrocarbons that have more carbon atoms than hydrocarbons that are present in the intermediate stream in a majority. This process is shown in FIG. 5, where the naphtha feedstream 402 is passed to a fractionation unit 400, generating a first stream 404 and a second stream 406. The second stream 406 is passed to a second fractionation unit 410 where an intermediate stream 412 and a heavy stream 414 are generated. The heavy stream 414 is passed to a second reformer. The second reformer includes at least two reformers 431 and 433, and can include more reformers in series, where the heavy stream 414 passes through in a sequential manner. The reformers 431 and 433 are operated at the same reaction conditions. The intermediate stream 412 is passed to the last 433 of the second reformer series. The second reformer series generates a second reformer effluent stream 436. The first stream 404 and the second reformer effluent stream 436 are passed to a first reformer 420, which is operated at a first inlet temperature as set forth above.

The first reformer 420 generates an effluent stream 422. The effluent stream 422 is passed to a light hydrocarbon stripping unit 460 where light gases and light hydrocarbons are removed from the effluent stream 422 generating a bottoms stream 462. The bottoms stream 462 is passed to a reformate stripper 450 where an overhead stream 452 comprising C6 to C8 aromatics is generated and a bottoms stream comprising C9+ aromatics. The overhead stream 452 is passed to an aromatics recovery unit 440 where an aromatics product stream 442 is generated and a raffinate stream 444 is generated.

Alternate embodiments include a process utilizing a plurality of reformers, where catalyst is passed in a series manner from a first reformer to a second reformer, and on through subsequent reformers. A hydrocarbon feedstream is fractionated to create a first feedstream comprising C6 and C7 hydrocarbons and a second feedstream comprising C8 and greater hydrocarbons. The splitting of the naphtha feedstream into different streams is subject to many variables. One factor is the makeup of the naphtha feedstream such as the naphthenic and olefinic content in the feedstream. Other factors can include decisions regarding operating temperatures for the different reformers.

The separation of the feeds to process the different feeds through different reformers produces an increase in the aromatics yields. The passing of an effluent stream from one reformer to another reformer can include passing the effluent stream to an intermediate reactor within the reformers. It is intended that the reformers include multiple reactor beds within the reformers. This allows for flexibility to control the residence time of the process streams passed to the reformers.

The reforming process is a common process in the refining of petroleum, and is usually used for increasing the amount of gasoline. The reforming process comprises mixing a stream of hydrogen and a hydrocarbon mixture and contacting the resulting stream with a reforming catalyst. The usual feedstock is a naphtha feedstock and generally has an initial boiling point of about 80° C. and an end boiling point of about 205° C. The reforming reactors are operated with a feed inlet temperature between 450° C. and 540° C. The reforming reaction converts paraffins and naphthenes through dehydrogenation and cyclization to aromatics. The dehydrogenation of paraffins can yield olefins, and the dehydrocyclization of paraffins and olefins can yield aromatics.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

Experiments were run using different feed compositions. In particular, using a 0.20% platinum R-26X catalyst at various reaction temperatures, coke formation on the catalyst for different feedstreams is shown below in Table 1. The results were generated by operating a microreactor at the listed temperatures at a hydrogen to hydrocarbon molar feed ratio of 5.0 and a deactivation cycle including four consecutive pressures of 450, 275, 170 and 450 kPa. Each pressure cycle includes four consecutive WHSV cycles of 1.5, 3.0, 0.75 and 1.5 hr$^{-1}$ for 3 hours at each WHSV. The values set forth in TABLE 1 represent percent coke based on the total weight of the catalyst:

TABLE 1

| | Temp., ° C. | | | |
|---|---|---|---|---|
| | 515 | 530 | 545 | 560 |
| 75 mol % n-C6* | 2.76 | 4.90 | 6.60 | 8.80 |
| 75 mol % n-C7* | 1.91 | 3.40 | 4.10 | 6.90 |
| 75 mol % n-C8* | 2.08 | 2.74 | 3.21 | 4.40 |
| 50 mol % MCP* | 9.20 | 11.00 | 12.50 | 16.20 |

*balance of feed is xylenes for n-C6, n-C7, and MCP feeds, and toluene for n-C8 feed Another set of experiments were performed. In this set of experiments, the experimental conditions to a microreactor included an inlet temperature of 515° C. to 560° C., a hydrogen to hydrocarbon ratio of 5, pressures in the reactor at different levels from 10 to 50 psig, or 170 to 450 kPa, the WHSV ranged from 0.75 hr$^{-1}$ to 3 hr$^{-1}$, and with different catalyst loadings to expand the conversion range.

TABLE 2

Feeds to Microreactors 1  75% n-hexane, 25% xylene - C6 conversion and selectivity
2  75% n-heptane, 25% xylene - C7 conversion and selectivity
3  75% n-octane, 25% xylene - C8 conversion and selectivity
4  50% MCP, 50% xylene - ring opening and expansion
5  50% MCP, 25% MCH, 25% xylene - C6 conversion and efficiency with an 'easy' C7
6  50% MCP, 25% n-heptane, 25% xylene - C6 conversion and efficiency with a 'hard' C7

MCP is methylcyclopentane, and MCH is methylcyclohexane. Easy and hard refer to the ability of the dehydrogenation and cyclization of the hydrocarbon. The aromatics are added to the feed for strong adsorption site effects.

The results are presented in Table 3, showing a summary of some of the experiments.

TABLE 3

| Feed | Conversion, % | Heavies, % | % C |
|---|---|---|---|
| 1 | 71.30 | 0.39 | 5.60 |
| 2 | 81.00 | 0.11 | 6.40 |
| 3 | 95.30 | 0.03 | 3.70 |
| 4 | 20.30 | 1.10 | 13.30 |
| 5 MCP | 32.60 | 0.37 | 11.80 |
| 5 MCH | 43.30 | — | — |
| 6 MCP | 48.40 | 0.30 | 10.00 |
| 6 n-C7 | 43.20 | — | — |

Additional results are provided to illustrate the effect of pressure, reaction temperature, and hydrogen to hydrocarbon ratio on yields of aromatics. In particular, additional sets of experiments were conducted using the second feed composition from Table 2 above, with reaction temperature varied at two different pressures and with hydrogen to hydrocarbon ratios varied at different pressures. Table 4 illustrates toluene yield across different reaction temperatures at a higher pressure (i.e., 450 kPa) and at a lower pressure (i.e., 170 kPa), with other experimental variables being the same as set forth above for the data generated in Table 1. Table 5 illustrates toluene yield at a higher pressure (i.e., 450 kPa) and at a lower pressure (i.e., 170 kPa) when hydrogen to hydrocarbon ratios are varied, with other experimental variables being the same as set forth above for the data generated in Table 1 except that a 0.25% platinum R-26X catalyst was used.

TABLE 4

| Temperature, ° C. | Toluene Yield, mol % at 450 kPa | Toluene Yield, mol % at 170 kPa |
|---|---|---|
| 515.00 | 55.04 | 69.35 |
| 530.00 | 64.55 | 77.71 |
| 545.00 | 70.27 | 73.58 |
| 560.00 | 68.86 | 59.37 |

TABLE 5

| | Toluene Yield, mol % |
|---|---|
| 450 kPa, 5 mol H2/Hydrocarbon | 63.66 |
| 450 kPa, 3 mol H2/Hydrocarbon | 71.35 |
| 275 kPa, 5 mol H2/Hydrocarbon | 73.26 |
| 170 kPa, 5 mol H2/Hydrocarbon | 74.92 |

The % C is the resulting carbon, or coke, deposited on the catalyst during the experiment, the conversion is the conversion of the alkane to an aromatic, and the heavies are the undesired heavier by-products generated in the reactor. As expected, the results indicated lower pressure improves aromatics selectivity, and increasing temperature improves conversion. But increasing temperature also increases cracking, which is undesired and increases methane generation. However, it was also found, and unexpected, that short times for the lighter alkanes, that is hexane, over heavier alkanes C8 and heavier was a factor. This was contrary to what was predicted as hexane is much more difficult to aromatize than C8 and heavier alkanes, and it was predicted that a longer reaction time was needed.

Heavier hydrocarbons should also be reacted at lower temperatures, as it was found that at higher temperatures hydrogenolysis of toluene to benzene and methane became significant. This reduces the value of the product and increases losses due to methane production. Therefore, increases can be achieved through innovative flow schemes that allow for process control of the reactions.

Based upon the results shown in Table 4, reactions conducted at lower pressures result in higher toluene yield as compared to reactions that are conducted at higher pressures at equivalent reaction temperatures. Further, based upon the results shown in Table 5, reactions conducted at lower hydrogen to hydrocarbon feed ratios result in higher toluene yield as compared to reactions that are conducted at higher hydrogen to hydrocarbon feed ratios at equivalent pressures. Yield results for benzene generally exhibit the same relationships to pressure and hydrogen to hydrocarbon feed ratio as shown above for toluene. It is also to be appreciated that the reactions conducted in the microreactor exhibit a slightly different dynamic than in actual industrial equipment, with the reactions in the microreactor being more isothermal than an industrial reactor (which generally runs under more adiabatic conditions). As such, it is to be appreciated that the yields at temperatures in the above experiments would be expected to be achieved with the temperatures being average bed temperatures in industrial reactors, with inlet temperatures of the industrial reactors being higher, e.g., 10-15° C. higher, than the average bed temperature.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing aromatics from a naphtha feedstream comprising:
    passing the feedstream to a fractionation unit, thereby generating a first stream comprising hydrocarbons having less than 8 carbon atoms and a second stream comprising hydrocarbons having at least 8 carbon atoms;
    passing the first stream to a first reformer to generate a first product stream, wherein the first reformer is operated at a first set of reaction conditions and wherein the first set of reaction conditions includes a first temperature and a first pressure, wherein the first temperature is greater than 545° C. and the first pressure is less than 310 kPa;
    passing the second stream to a second reformer to generate a second product stream, wherein the second reformer is operated at a second set of reaction conditions, wherein the second set of reaction conditions includes a second temperature and a second pressure, wherein the first pressure is lower than the second pressure, wherein the second temperature is less than 540° C. and wherein the second pressure is less than 500 kPa;
    passing the first product stream and the second product stream to an aromatics separation unit;
    wherein the first set of reaction conditions and the second set of reaction conditions include contacting the feedstream with a catalyst, where the catalyst comprises a Group VIII noble metal on a support.

2. The process of claim 1, wherein the first temperature is from about 545° C. to about 560° C., and wherein the first reformer is operated at the first temperature of from about 545° C. to about 560° C.

3. The process of claim 1, wherein the second temperature is less than 540° C., and wherein the second reformer is operated at the second temperature of less than 540° C.

4. The process of claim 3, wherein the second temperature is from about 520° C. to less than 540° C., and wherein the second reformer is operated at the second temperature of from about 520° C. to less than 540° C.

5. The process of claim 1, wherein the first pressure is from about 130 kPa to 310 kPa, and wherein the first reformer is operated at the first pressure of from about 130 kPa to 310 kPa.

6. The process of claim 5, wherein the second pressure is from about 240 kPa to 580 kPa, and wherein the second reformer is operated at the second pressure of from about 240 kPa to 580 kPa, provided the first pressure is lower than the second pressure.

7. The process of claim 1, wherein the first set of reaction conditions further includes a first hydrogen to hydrocarbon feed ratio, wherein the second set of reaction conditions further includes a second hydrogen to hydrocarbon feed ratio greater than the first hydrogen to hydrocarbon feed ratio, and wherein the second reformer is operated at the second hydrogen to hydrocarbon feed ratio greater than the first hydrogen to hydrocarbon feed ratio.

8. The process of claim 7, wherein the first hydrogen to hydrocarbon feed ratio is a mole ratio of from about 0.1 to about 10 and wherein the first reformer is operated at the first hydrogen to hydrocarbon feed ratio of from about 0.1 to about 10.

9. The process of claim 8, wherein the first hydrogen to hydrocarbon feed ratio is a mole ratio of from about 0.2 to about 2 and wherein the first reformer is operated at the first hydrogen to hydrocarbon feed ratio of from about 0.2 to about 2.

10. The process of claim 1, wherein the second reformer comprises at least two reactors, wherein the second stream passes sequentially through the reactors, and wherein the second reformer further comprises heating units between successive reactors.

11. The process of claim 1, wherein the first reformer comprises at least two reactors, wherein the first stream is further split and separately passed through the reactors.

12. The process of claim 1, wherein the first set of reaction conditions further includes a conversion per pass rate for hydrocarbons having 6 carbon atoms, and wherein the first reformer is operated at a conversion per pass rate for hydrocarbons having 6 carbon atoms of from about 33% to about 50%.

13. The process of claim 12, wherein passing the first product stream to the aromatics separation unit creates an aromatics product stream and a raffinate stream comprising unconverted hydrocarbons having 6 carbon atoms.

14. The process of claim 13, further comprising recycling the raffinate stream to the first reformer.

15. The process of claim 1, further comprising increasing pressure of the first product stream prior to passing the first product stream to the aromatics separation unit.

16. A process for producing aromatics from a naphtha feedstream comprising:
    passing the feedstream to a fractionation unit, thereby generating a first stream comprising hydrocarbons having less than 8 carbon atoms and a second stream comprising hydrocarbons having at least 8 carbon atoms;

passing the first stream to a first reformer to generate a first product stream, wherein the first reformer is operated at a first set of reaction conditions and wherein the first set of reaction conditions includes a first temperature, a first pressure, a first hydrogen to hydrocarbon feed ratio, and a conversion per pass rate for hydrocarbons having 6 carbon atoms, wherein the first pressure is less than 310 kPa, and the first temperature is greater than 545° C.;

passing the second stream to a second reformer to generate a second product stream, wherein the second reformer is operated at a second set of reaction conditions, wherein the second set of reaction conditions includes a second temperature, a second pressure, and a second hydrogen to hydrocarbon feed ratio, wherein the first temperature is greater than the second temperature, wherein the first pressure is lower than the second pressure, and wherein the second hydrogen to hydrocarbon feed ratio greater than the first hydrogen to hydrocarbon feed ratio, wherein the second pressure is less than 500 kPa and wherein the second temperature is less than 540° C.;

passing the first product stream and the second product stream to an aromatics separation unit;

wherein the first set of reaction conditions and the second set of reaction conditions include contacting the feedstream with a catalyst, where the catalyst comprises a Group VIII noble metal on a support.

17. The process of claim 16, wherein the first temperature is greater than 530° C., wherein the first pressure is from about 130 kPa to 310 kPa, wherein the first hydrogen to hydrocarbon feed ratio is a mole ratio of from about 0.2 to about 2, and wherein the first reformer is operated at the first temperature of greater than 530° C., the first pressure of from about 130 kPa to 310 kPa, and the first hydrogen to hydrocarbon feed ratio of from about 0.2 to about 2.

18. The process of claim 16, wherein the first reformer is operated at a conversion per pass for hydrocarbons having 6 carbon atoms of from about 33% to about 50%.

19. A process for producing aromatics from a naphtha feedstream comprising:

passing the feedstream to a fractionation unit, thereby generating a first stream comprising hydrocarbons having less than 8 carbon atoms and a second stream comprising hydrocarbons having at least 8 carbon atoms;

passing the first stream to a first reformer to generate a first product stream, wherein the first reformer is operated at a first set of reaction conditions and wherein the first set of reaction conditions includes a catalyst, a first temperature and a first pressure, wherein the first pressure is less than 310 kPa, and the first temperature is greater than 545° C.;

passing the second stream to a second reformer to generate a second product stream, wherein the second reformer is operated at a second set of reaction conditions, wherein the second set of reaction conditions includes a catalyst a second temperature and a second pressure, wherein the first temperature is greater than the second temperature and wherein the first pressure is lower than the second pressure, wherein the second pressure is between 240 kPa and 500 kPa and wherein the second temperature is less than 540° C.;

passing the first product stream to a compressor; and passing the first product stream and the second product stream to an aromatics separation unit, wherein the first product stream is passed to the aromatics separation unit from the compressor and wherein the second product stream is passed to the aromatics separation unit in the absence of further pressurizing;

wherein the catalyst in the first reformer and the catalyst in the second reformer are the same catalyst.

* * * * *